United States Patent
Suzuki et al.

(10) Patent No.: US 7,841,237 B2
(45) Date of Patent: Nov. 30, 2010

(54) ULTRASONIC TESTING APPARATUS FOR TURBINE FORKS AND METHOD THEREOF

(75) Inventors: Yutaka Suzuki, Hitachi (JP); Masahiro Koike, Hitachi (JP); Tetsuya Matsui, Hitachi (JP); Kojirou Kodaira, Hitachinaka (JP); Katsumi Isaka, Mito (JP); Mitsuru Odakura, Hitachi (JP); Kenji Tayama, Mito (JP); Kazuhiro Suzuki, Hitachi (JP); Kenji Kumasaka, Hitachi (JP); Yuuji Adachi, Hitachi (JP)

(73) Assignees: Hitachi, Ltd., Tokyo (JP); Hitachi Engineering & Services Co., Ltd., Ibaraki (JP)

( * ) Notice: Subject to any disclaimer, the term of this patent is extended or adjusted under 35 U.S.C. 154(b) by 339 days.

(21) Appl. No.: 11/862,871

(22) Filed: Sep. 27, 2007

(65) Prior Publication Data

US 2009/0120192 A1    May 14, 2009

(30) Foreign Application Priority Data

Sep. 29, 2006    (JP) .............................. 2006-266254

(51) Int. Cl.
    *G01N 29/04* (2006.01)
(52) U.S. Cl. .............................. 73/623; 73/584; 73/593; 73/620
(58) Field of Classification Search .................. 73/584, 73/593, 579, 620, 622, 623, 660
    See application file for complete search history.

(56) References Cited

U.S. PATENT DOCUMENTS 4,887,648 A * 12/1989 Cunnane ............... 139/383 AA
5,239,218 A * 8/1993 Hashimoto et al. ........ 310/68 B
5,445,027 A * 8/1995 Zorner ......................... 73/593
5,942,690 A * 8/1999 Shvetsky ...................... 73/660
6,668,651 B2 * 12/2003 Beausseroy et al. ........... 73/579
7,428,842 B2 * 9/2008 Fair et al. ...................... 73/626
7,543,506 B2 * 6/2009 Merendino, Sr. ............. 73/779

FOREIGN PATENT DOCUMENTS

| JP | 57-120858 | 7/1982 |
| JP | 62-261955 | 11/1987 |
| JP | 2000-214136 | 8/2000 |
| JP | 2002-090348 | 3/2002 |
| JP | 2002-310998 | 10/2002 |

OTHER PUBLICATIONS

D Reilly et al, "On the Use of 3D Ray-Tracing and Beam Simulation for the Design of Advanced UT Phased Array Inspection Techniques", Proceeding of the Fifth Intl. Conference on NDE in Relation to Structural Integrity for Nuclear and Pressurized Components, pp. 322-331, (May 10-12, 2006).

* cited by examiner

*Primary Examiner*—J M Saint Surin
(74) *Attorney, Agent, or Firm*—Mattingly & Malur, P.C.

(57) ABSTRACT

An ultrasonic testing apparatus for a turbine fork of a turbine blade joined to a turbine disc, comprising:
  an ultrasonic testing sensor;
  a sensor mounting apparatus for mounting the ultrasonic testing sensor on a flat portion on a side surface of the turbine fork with the turbine blade joined to the turbine disc; and
  an ultrasonic testing apparatus for inspecting internal and external surfaces of the turbine fork by using reflected waves, which is received by the ultrasonic testing sensor, from the internal surface of the turbine fork.

7 Claims, 13 Drawing Sheets

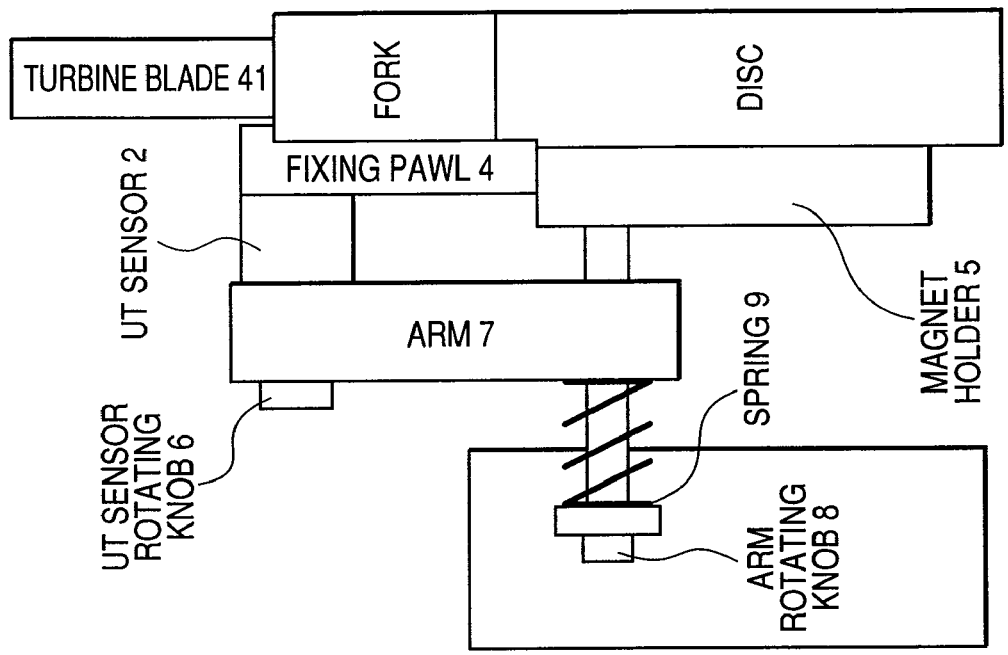
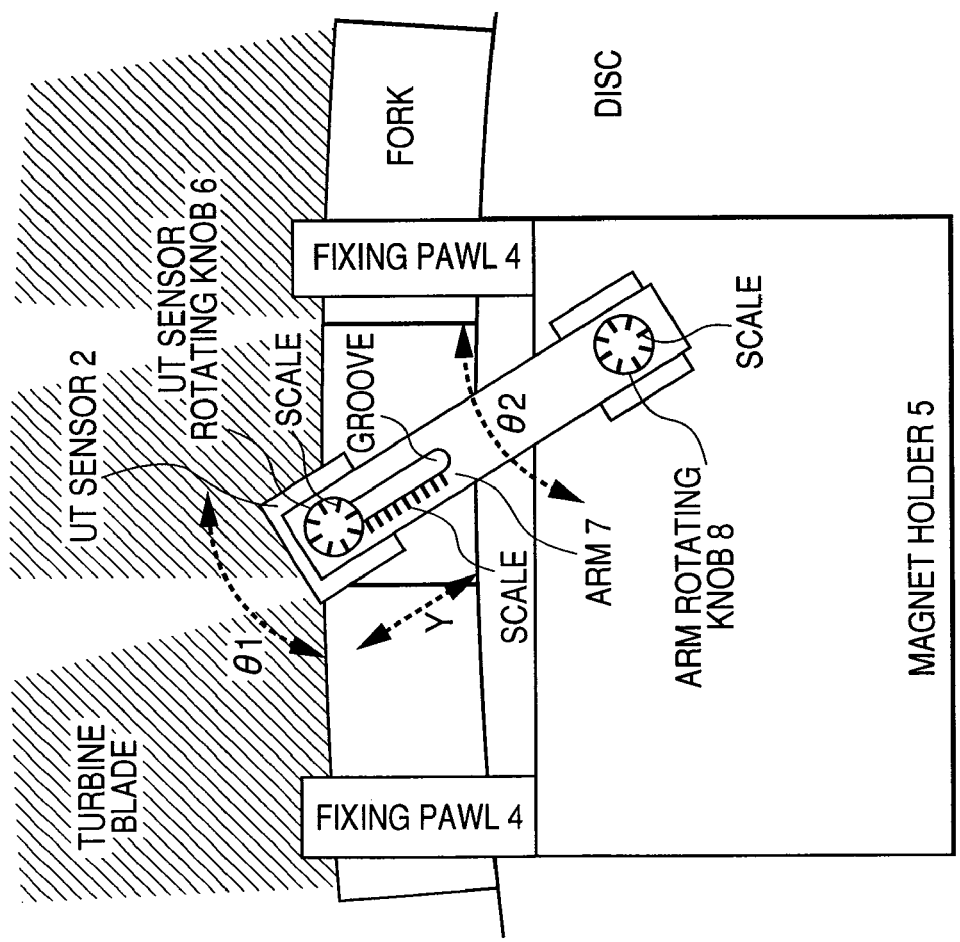
FIG. 2B SIDE VIEW
FIG. 2A FRONT VIEW

TURBINE

JOINT BETWEEN THE DISC AND TURBINE BLADES

DEFECTS ON A FORK

PROBLEM WHEN A SENSOR IS MOUNTED ON A BLADE

PROBLEM WHEN A SENSOR IS MOUNTED ON A SIDE

ULTRASONIC TESTING APPARATUS FOR TURBINE FORKS AND METHOD THEREOF

CLAIM OF PRIORITY

The present application claims priority from Japanese application serial no. 2006-266254, filed on Sep. 29, 2006, the content of which is hereby incorporated by reference into this application.

BACKGROUND OF THE INVENTION

The present invention relates to an ultrasonic testing apparatus and method thereof that are suitable for shortening time taken to inspect turbine forks.

To facilitate the manufacturing and maintenance of a turbine used in a power generating plant, its rotor and turbine blades are manufactured separately, and the structural portions of the forks of the turbine blades are inserted to the disc on the rotor and fixed by inserting pins into holes formed in the forks, as shown in FIGS. 15A and 15B. As the turbine rotates, stress is generated to the fork holes, generating cracks at locations as shown in FIG. 15C.

In conventional inspection for cracks in the fork holes, the turbine blades are taken off and magnetic particle testing (hereinafter referred to as MT) is then performed.

The MT is a method for detecting a leak of a magnetic flux from a defect when a magnetic field is applied to a test object as illustrated in FIG. 16. Ultraviolet rays are irradiated to magnetic metal particles on which a fluorescent material is applied, the fluorescent material being accumulated by the magnetic flux that leaks from the defect. Whether the magnetic metal particles is accumulated can be determined by observing whether there is fluorescent light, and thus whether there is a defect can be determined. In inspection for fork hole defects based on the MT, since it is necessary to pull out pins and to separate the turbine blades from the disc, it is a problem that time of the inspection lengthens.

Accordingly, in fork hole inspection, there is an approach to ultrasonic testing (hereinafter referred to as UT). The UT is a method for sending an ultrasonic wave to a test object and receiving a reflected wave. Whether there is a defect can be determined on the basis of whether there is the reflected wave from the defect. If a UT sensor is placed at the root of the blade to make an ultrasonic wave directly incident to a place of a defect as shown in FIG. 17A, a spacing is left between the fork and the UT sensor because the location at which the sensor is placed is curved. As a result, it becomes difficult to make an ultrasonic wave incident. If the UT sensor may be placed on a side surface of a fork as shown in FIG. 17B so that an ultrasonic wave reflects in the fork and the reflected ultrasonic wave is incident to a place of a defect, it is difficult to locate a place of a testing because the incident path of the ultrasonic wave is not clear. Therefore, the UT inspection is not used in practical applications. Japanese Patent Laid-open No. 2002-310998 discloses ultrasonic testing technology applied to embedded parts that are not fork-shaped.

SUMMARY OF THE INVENTION

As described above, non-destructive inspection targeted at embedded fork portions having complex shapes has not been considered.

An object of the present invention is to achieve non-destructive inspection of turbine forks without having to disassemble them.

The main feature of the present invention is to provide a sensor mounting tool for restricting the degree of freedom of UT sensor motion to rotation and parallel motion or a sensor moving apparatus for controlling the rotation and parallel motion of the UT sensor by using actuators and to identify a reflected wave coming from a defect by comparing ultrasonic testing signals with reference signals being geometric echoes.

A ultrasonic testing apparatus for turbine forks and method thereof of the present invention shorten inspection time because inspection is performed without the turbine blades and disc having to be separated.

BRIEF DESCRIPTION OF THE DRAWINGS

FIGS. 2A and 2B are a structural diagram showing a UT sensor mounting tool according to the embodiment 1; FIG. 2A is a front view of the UT sensor mounting tool; FIG. 2B is a side view of the UT sensor mounting tool.

FIG. 15A is a perspective view of the turbine; FIG. 15B is a perspective view of the turbine fork; FIG. 15C is a expanded perspective view of the turbine fork.

FIG. 17A is a expanded perspective view of the turbine fork in a state that UT sensor is placed on the turbine fork; FIG. 17B is a side view (left) and a front view (right) of the turbine fork shown in FIG. 17A.

DETAILED DESCRIPTION OF THE PREFERRED EMBODIMENTS

In an ultrasonic testing method for turbine forks of turbine blades, by which the turbine blades are joined to a turbine disc, an ultrasonic testing sensor is mounted on a flat portion on a side surface of the turbine fork in a state that the turbine blades are joined to the turbine disc, and the ultrasonic testing sensor is used for ultrasonic testing of internal and external surfaces of the turbine fork by use of reflected waves from the internal surface of the turbine fork. Thus, the UT inspection can be performed without the turbine blade and turbine disc having to be separated.

To shorten the inspection time, a sensor mounting tool or sensor moving apparatus is provided to perform ultrasonic testing by sending and receiving ultrasonic waves from a side surface of the fork. This ultrasonic testing has a step for identifying a reflected wave from a defect of comparing ultrasonic testing signals with reference signal being geometric echoes by comparing ultrasonic testing signals with reference signal being geometric echoes.

Embodiment 1

A embodiment concerning ultrasonic testing of a fork, in which a UT sensor mounting tool is used, will be described according to FIGS. 1 to 6 and equation (1).

Figure 1:
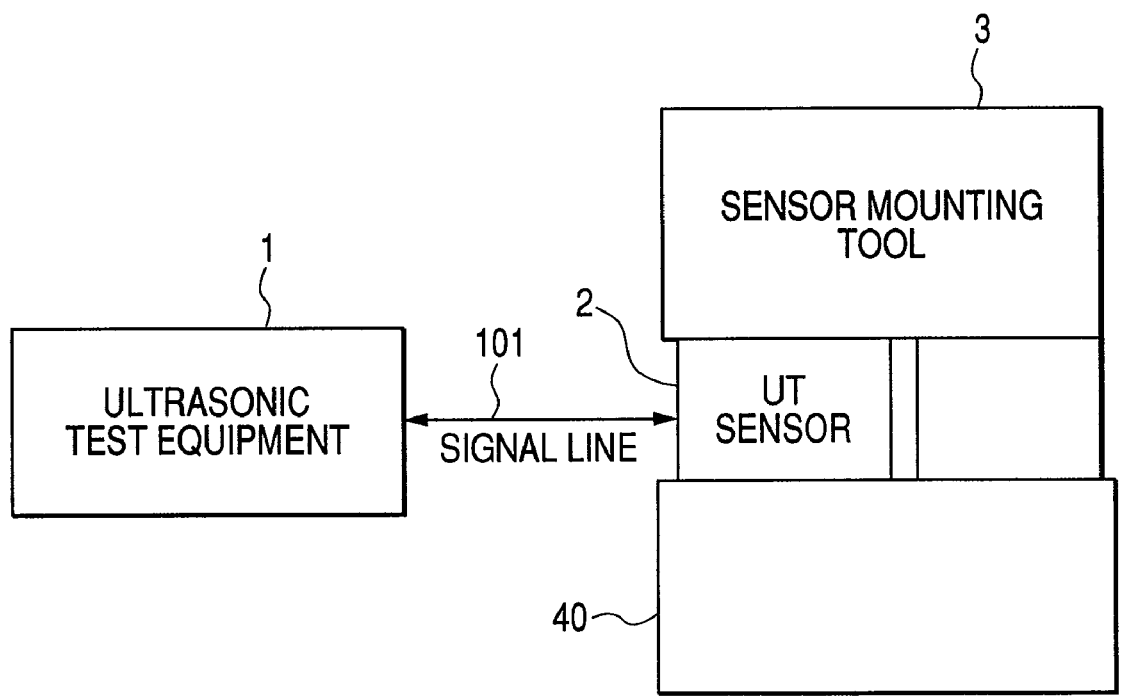
FIG. 1 is a structural diagram showing an ultrasonic testing apparatus for turbine forks according to a embodiment 1.

FIG. 1 is a structural diagram showing an ultrasonic testing apparatus according to a embodiment 1. The ultrasonic testing apparatus includes an ultrasonic test equipment 1, a UT sensor 2, a UT sensor mounting tool 3, and a signal line 101 connecting between the ultrasonic test equipment 1 and the UT sensor 2. The ultrasonic transmitting and receiving element of the UT sensor 2 uses a piezoelectric device based on PZT, $LiNbO_3$, PVDF, or the like. The signal line 101 is a copper wire covered with an insulator.

FIGS. 2A and 2B are a structural diagram showing a UT sensor mounting tool 3 according to the embodiment 1. The UT sensor mounting tool 3 is a sensor mounting means for mounting the UT sensor on a flat portion on a side surface of the turbine fork in a state that the turbine blades are joined to the turbine disc. The UT sensor mounting tool 3 has fixing pawls 4 for the blades, a magnet holder 5 for fixing the UT sensor mounting tool to the blades, a UT sensor rotating knob 6, a UT sensor fixing arm 7, an arm rotating knob 8, and a spring 9 for pressing the UT sensor 2 against a side surface of the fork together with the arm 7.

Since the UT sensor mounting tool 3 is provided, the sensor 2 can be appropriately mounted with ease on a flat portion on a side surface of the turbine fork. Since ultrasonic testing is performed for the flat side, the magnitudes of incident echoes can be equalized, enabling defects (flaws) to be appropriately detected.

The fixing pawls 4 are setted to the elementary part of the turbine blades 41 so that the UT sensor mounting tool 3 is fixed by means of the magnetic force of the magnet holder 5. The UT sensor 2 is screwed to the UT sensor rotating knob 6. When the UT sensor rotating knob 6 is rotated, the UT sensor 2 rotates in the θ1 direction in FIG. 2A.

The arm 7 is provided with a through-groove. Since the UT sensor rotating knob 6 is installed in such a way that it passes through the groove, the sensor can move in the Y direction in FIG. 2. The arm is turned in the θ2 direction in FIG. 2 around the arm rotating knob 8. The incident direction of the ultrasonic wave can be quantified by graduating in the UT sensor rotating knob 6, arm 7 and arm rotating knob 8. The fixing pawls 4, arm 7, sensor rotating knob 6 and arm rotating knob 8 are molded with metal or plastic. The spring 9 being an elastic body, is made of CrMo steel, Mo steel, or another steel having a large elastic coefficient.

Since a means for rotating the ultrasonic testing sensor 2 is provided as described above, the sensor 2 can be appropriately mounted with ease on a flat portion on a side surface of the turbine fork, and thereby mounting conditions can be set with ease during ultrasonic testing.

Figure 3:
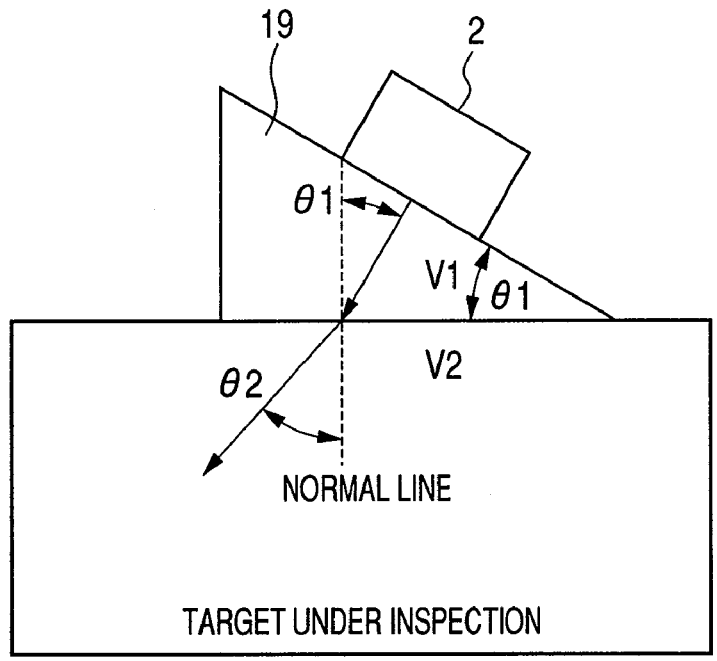
FIG. 3 is an explanatory drawing showing principle of changing the incident path of an ultrasonic wave by replacing a shoe.

An incident angle of an ultrasonic wave to the target under inspection is adjusted by providing a wedgy shoe 19 (acrylic) between the UT sensor 2 and the target under inspection. FIG. 3 illustrates the principle of incident angle adjustment for an ultrasonic wave by use of a shoe. The incident angle of an ultrasonic wave coming from the shoe to the target under inspection is represented by equation (1) according to the Snell's law.

$$\sin(\theta 1) \div V1 = \sin(\theta 2) \div V2 \quad (1)$$

V1: Ultrasonic velocity in the shoe

θ1: Incident angle of an ultrasonic wave from the shoe to the test object (=angle at the end of the shoe)

V2: Ultrasonic velocity in the test object

θ2: Incident angle of an ultrasonic wave in the test object

By screwing the shoe 19 of this type to the UT sensor 2, the incident angle of an ultrasonic wave can be adjusted.

Since the ultrasonic testing sensor 2 is used for ultrasonic testing of internal and external surfaces of the turbine fork by use of reflected waves from the internal surface of the turbine fork, it becomes possible to perform inspection without the turbine blade and turbine disc having to be separated.

Figure 6:
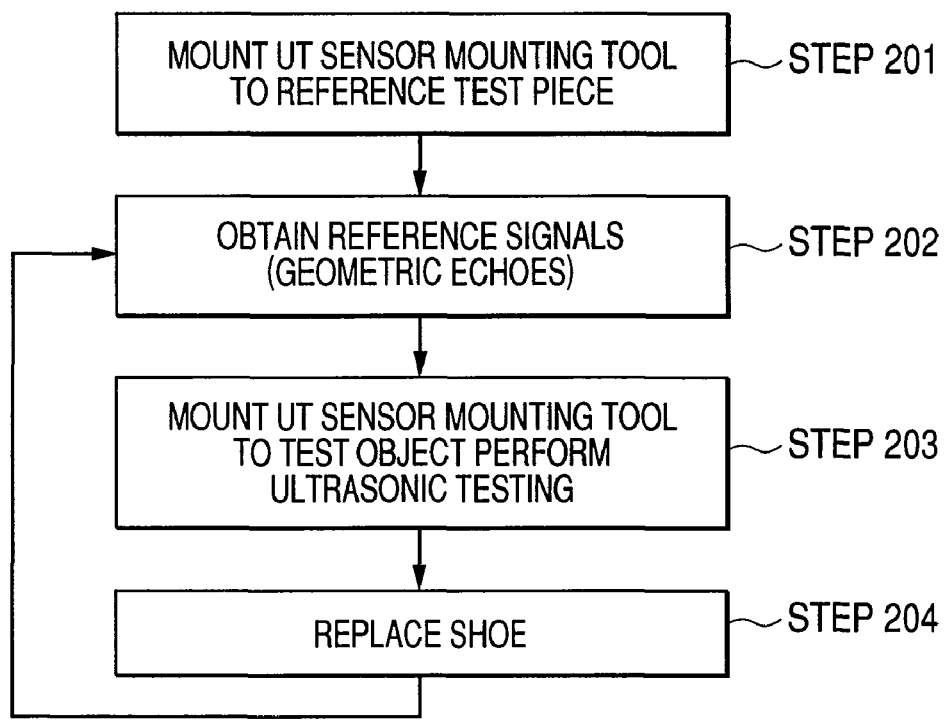
FIG. 6 is a flowchart showing procedure of an ultrasonic testing according to the first embodiment.

The ultrasonic testing steps in the embodiment 1, which are indicated in FIG. 6, will be described below, mainly for a sensor mounting procedure and ultrasonic testing procedure.

In step 201, the UT sensor mounting tool 3 is mounted to a reference test piece having no defect and the same size as the test object.

Figure 4:
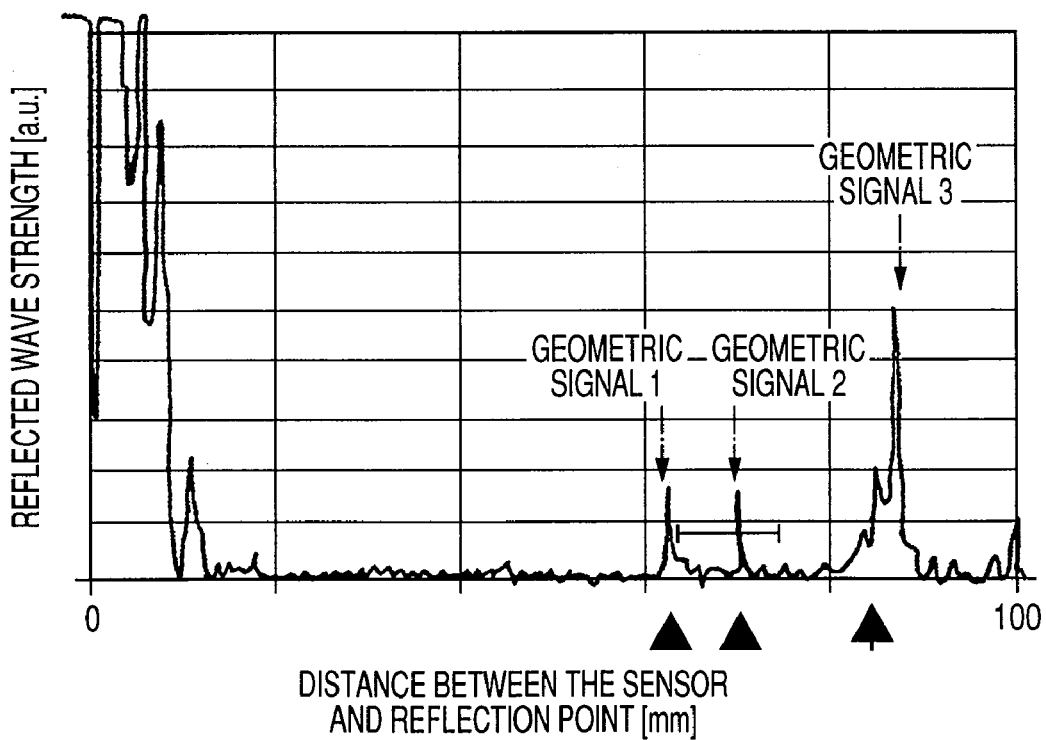
FIG. 4 is an explanatory drawing showing exemplary evaluation based on reference (geometric) signals.

In step 202, geometric echoes (reference echoes) reflected at concavities and convexities on the reference test piece as shown in FIG. 4 are obtained.

Figure 5:
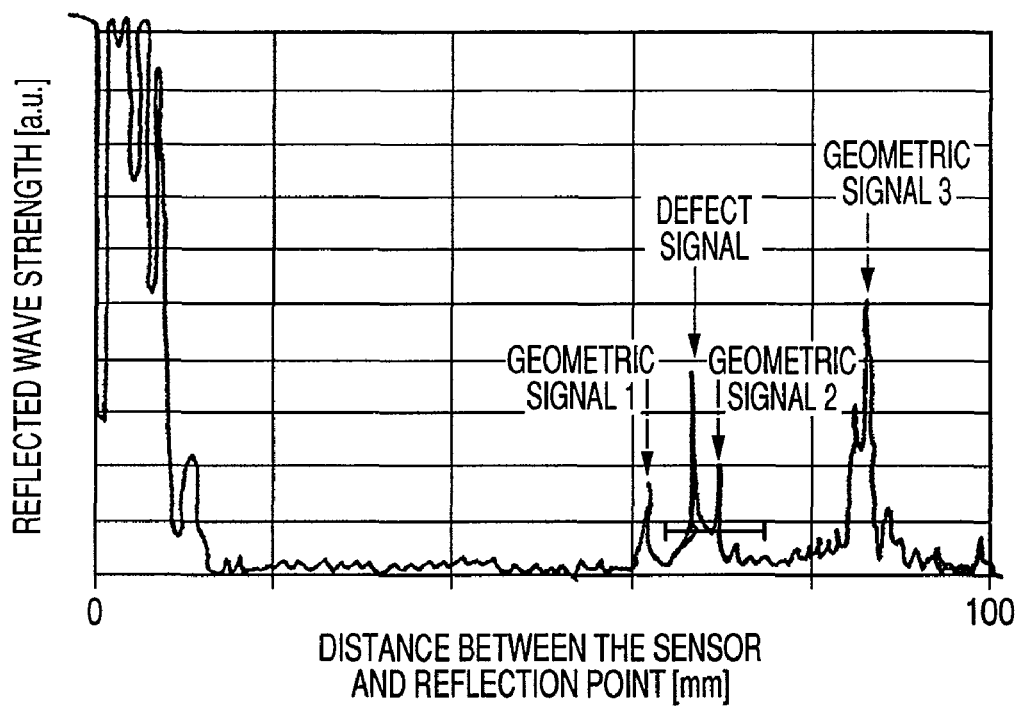
FIG. 5 is an explanatory drawing showing exemplary measurement of a defect signal.

In step 203, the UT sensor mounting tool 3 is mounted to the test object, ultrasonic testing is performed, and ultrasonic testing signals as shown in FIG. 5 are obtained. The obtained ultrasonic testing signals are compared with the reference signals in FIG. 4. The presence or absence of a defect is determined according to whether there is a reflected wave at a place other than the places where the reference echoes are reflected.

In step 204, the shoe is replaced to change the ultrasonic wave incident angle, that is, the place to which the ultrasonic wave is incident is changed.

As described above, the ultrasonic testing sensor is used for ultrasonic testing of internal and external surfaces of the turbine fork by use of reflected waves from the internal surface of the turbine fork, desired reflected ultrasonic waves generated in the turbine fork are used as reference signals, and a reflected wave from a defect is identified by comparing detected ultrasonic testing signals with the reference signals. Thus, it becomes possible to detect a defect in ultrasonic testing without the turbine blade and turbine disc having to be separated.

Furthermore, since an ultrasonic wave is made incident and skipped, problems with, for example, steps of the fork portion having a complex geometric can be avoided. An ultrasonic wave is also made incident from a side surface of the fork portion and skipped, both the internal surface and external surface of the fork portion can be inspected from the same testing surface.

In present embodiment with the structure described above, since the scale of the UT sensor mounting tool 3 is used to enable the quantification of the incident direction of the ultrasonic wave, the location at which an ultrasonic wave is incident can be determined. Furthermore, since the presence or absence of a defect signal is determined by using geometric echoes as the reference echoes, whether there is a defect can be easily determined. Accordingly, time taken to inspect the turbine fork can be shortened.

Embodiment 2

An embodiment of the present invention related to ultrasonic testing of turbine forks in which a UT sensor moving apparatus is used will be described according to FIGS. 7 to 14 and equations (2) to (5).

Figure 7:
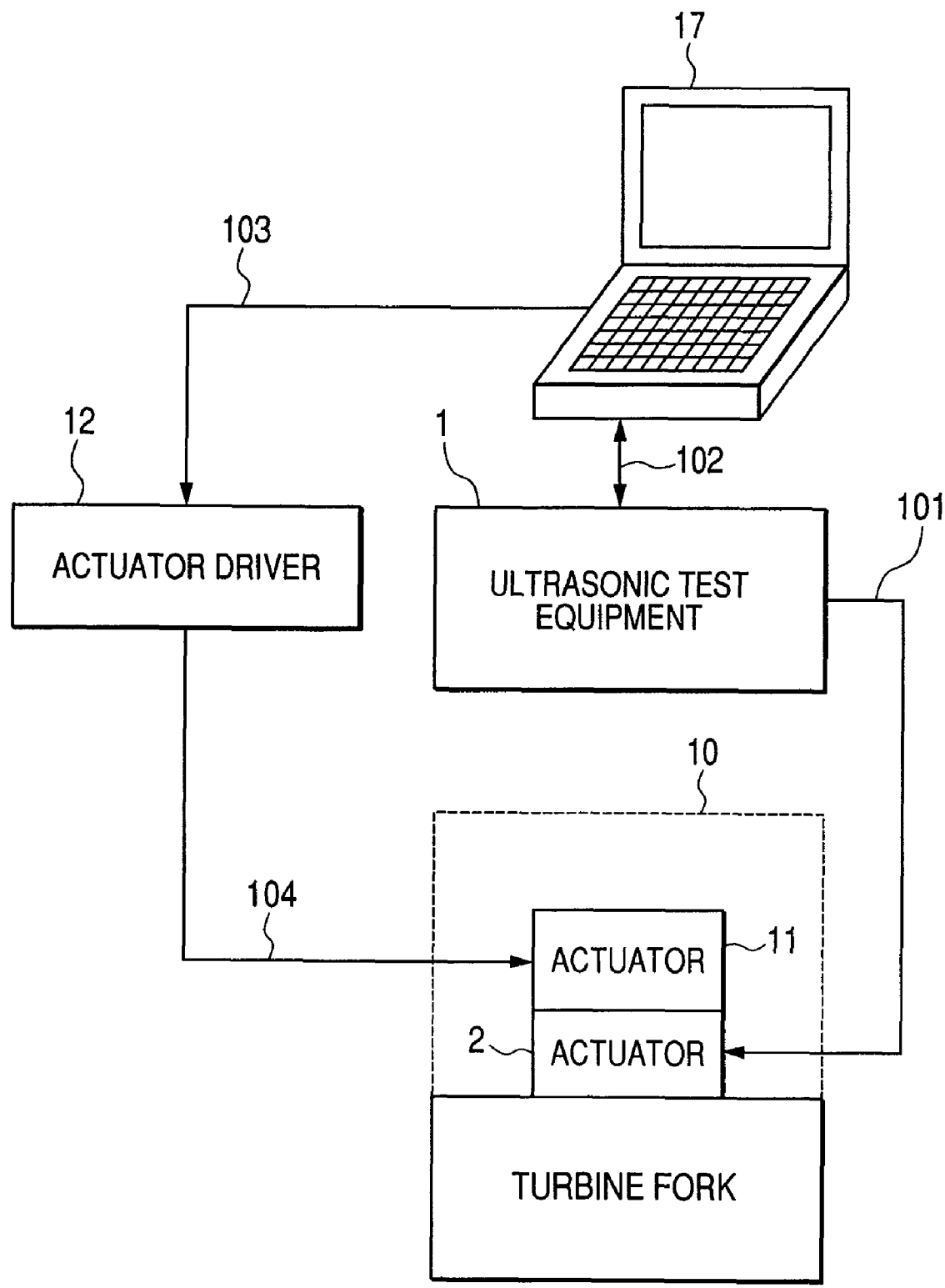
FIG. 7 is a structural diagram showing an ultrasonic testing apparatus for turbine forks according to a embodiment 2.

FIG. 7 is a structural diagram showing an ultrasonic testing apparatus for turbine forks according to a embodiment 2. The ultrasonic testing apparatus includes an ultrasonic test equipment 1, a UT sensor 2, a personal computer 17, a sensor moving aparatus 10, an actuator 11, an actuator driver 12, a signal line 101 connecting between the ultrasonic test equipment 1 and the UT sensor 2, a signal line 102 connecting between the personal computer 17 and the ultrasonic test equipment 1, a signal line 103 connecting between the personal computer 17 and the actuator driver 12, and a power line 104 connecting between the actuator 11 and the actuator driver 12. The signal lines and power line use copper wires covered with an insulator.

Figure 8:
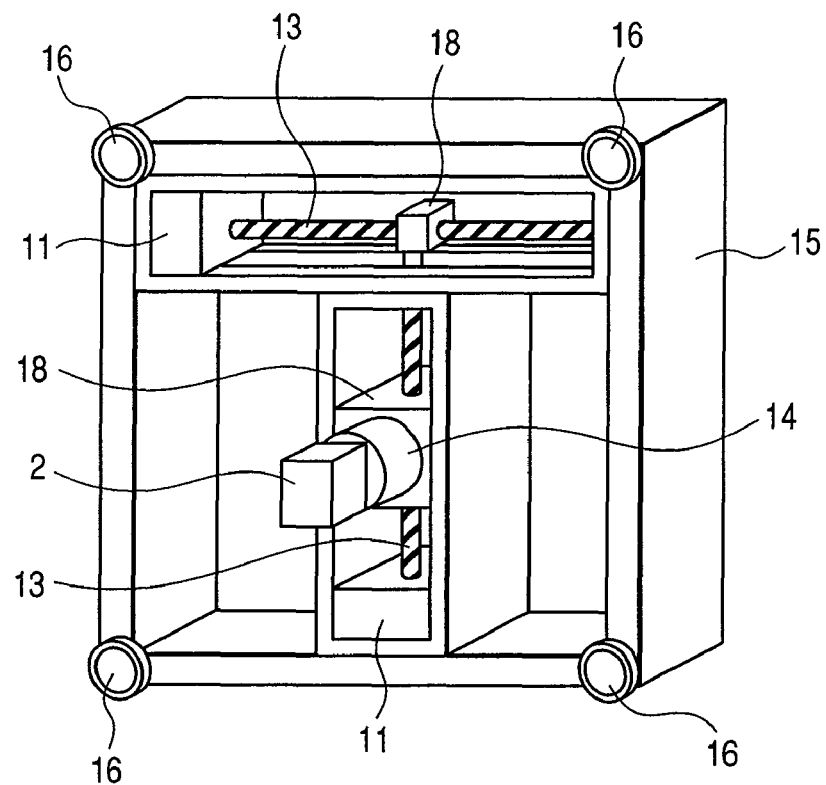
FIG. 8 is a structural diagram showing a UT sensor moving apparatus according to the embodiment 2.

FIG. 8 is a structural diagram showing a UT sensor moving apparatus according to the embodiment 2. The UT sensor moving apparatus is a means for translationally moving the ultrasonic testing sensor 2. This moving apparatus enables a plurality of turbine forks to be efficiently inspected, and is also suitable for automation. The UT sensor moving apparatus comprises the actuators 11, a movement rods 13 having threads formed on a outer surface for converting the rotation of the actuator 11 into parallel motion, a moving member 18 having threads formed on a inner surface for engaging with the movement rod so as to move the UT sensor 2 in parallel, an actuator-incorporating rotational stage 14 mounted on another moving member 18, a storage case 15 for storing the actuator and moving apparatses, and suction caps 16 for mounting the UT sensor moving apparatus to the elementary part of the turbine blade. The actuators use motors, ultrasonic actuators, or a combination of them. The movement rods 18 are made of CrMo steel, Mo steel, or another steel having a large elastic coefficient. The suction caps 16 are molded with resin. The storage case 14 is molded with metal or resin. The UT sensor 2 is screwed to the rotational stage 14 and thus the UT sensor can be rotationally moved. The rotational stage is screwed to another moving member 18 and another movement rod 13 is rotated by the actuator 11 so as to move the UT sensor 2 in parallel together with another moving member 18 combined with another movement rod 13.

Figure 9:
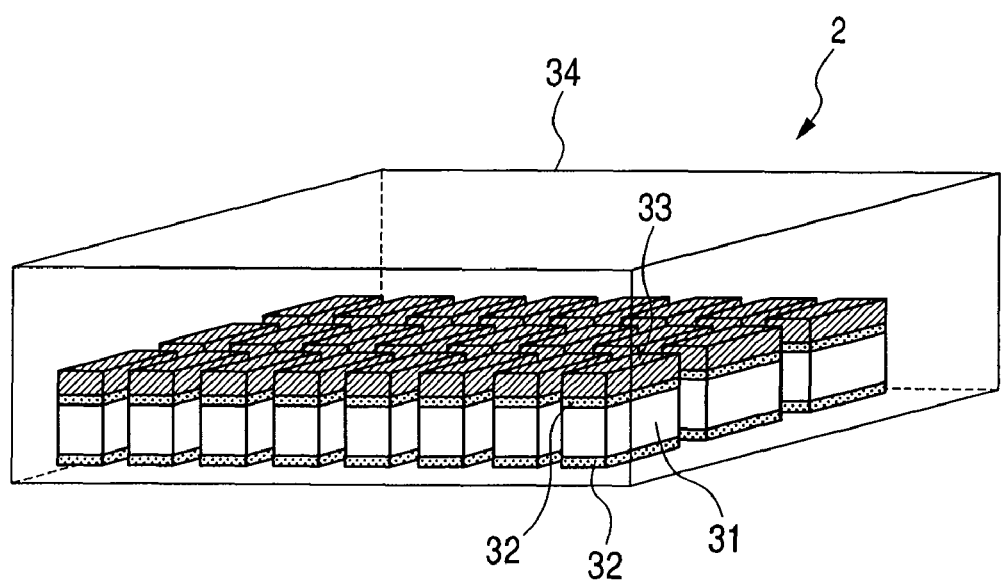
FIG. 9 is a structural diagram showing the UT sensor according to the embodiment 2.

FIG. 9 is a structural diagram showing the UT sensor being used in the embodiment 2. The UT sensor 2 is an array sensor is used as the UT sensor, in which a plurality of rows of ultrasonic elements 31 are housed in a protective case 34, a plurality of ultrasonic being disposed in each row. Electrodes 32 are deposited on both ends of the ultrasonic element 31, and connected to a signal line 101 connecting between the UT sensor 2 and the ultrasonic test equipment 1. A dumper 33 is provided on the end opposite to the region in contact with the test object. The dumper 33 reduces ultrasonic element vibration generated after ultrasonic oscillation. The ultrasonic element 31 uses a piezoelectric device based on PZT, $LiNbO_3$, PVDF, just like in the embodiment 1. The electrode 32 is made of silver, gold, copper, or another metal with high conductivity. The dumper 33 is made of a mixture of resin and heavy metal such as Ta, W, or Hf. The protective case 34 is molded with metal or resin.

Figure 10:
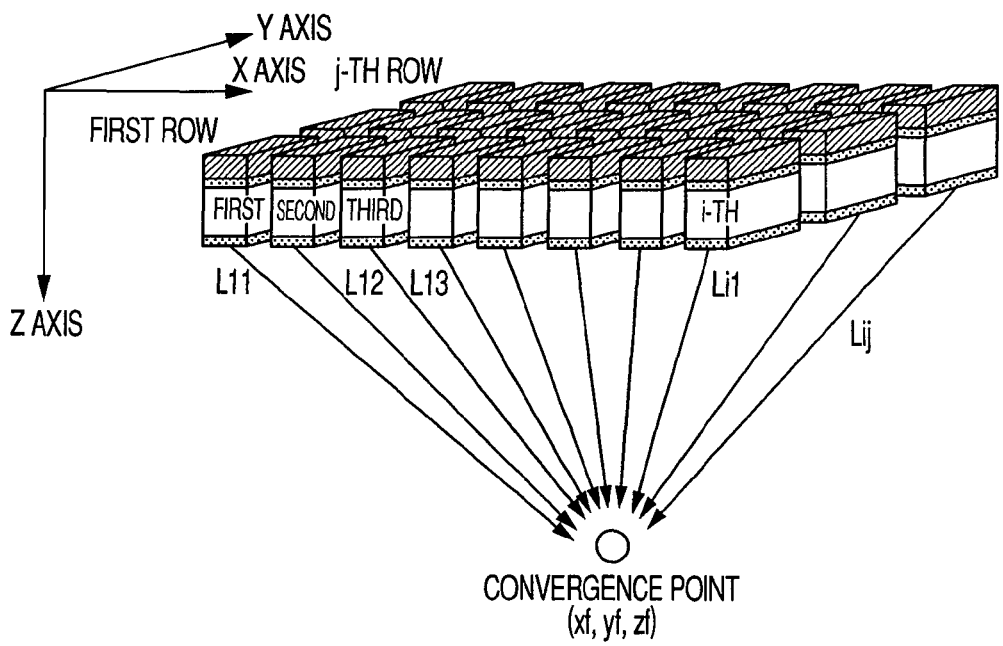
FIG. 10 is an explanatory drawing showing an ultrasonic testing method according to the embodiment 2.
Figure 11:
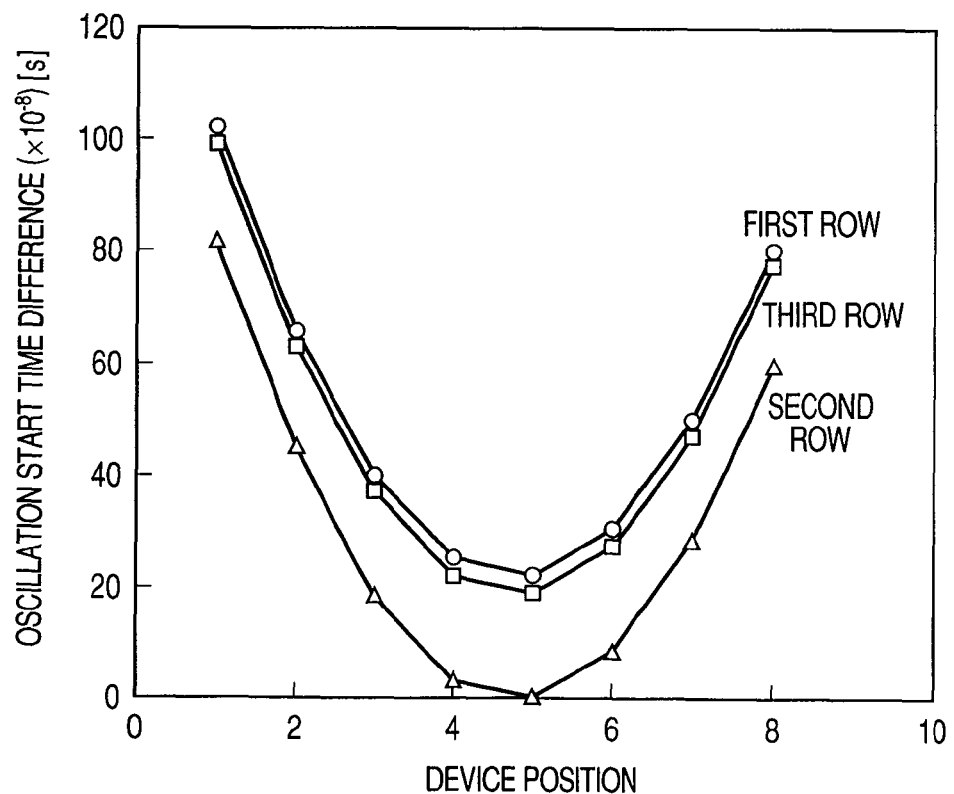
FIG. 11 is an explanatory drawing showing an example of differences in time at which ultrasonic oscillation starts.

FIG. 10 illustrates an ultrasonic testing method in which the above UT sensor 2 is used. Differences in time at which ultrasonic oscillation starts are adjusted according to equations (2) and (3) so that ultrasonic waves from all ultrasonic elements 31 arrive at a focus point at the same time.

$$dt = (\max(L) - Li) \div V \quad (2)$$

$$Lij = ((xij - xf)^2 + (yij - yf)^2 + (zf)^2)^{1/2} \quad (3)$$

max (L): Maximum distance [m] between the element and the focus point
Lij: Distance [m] between the i-th device in the j-th row and the focus point
V: Ultrasonic velocity [m/s]
xij: x coordinate [m] of the i-th element in the j-th row
xf: x coordinate [m] of the focus point
yij: y coordinate [m] of the i-th element in the j-th row
yf: y coordinate [m] of the focus point
zf: z coordinate [m] of the focus point FIG. 11 illustrates an example of differences in time at which ultrasonic oscillation starts. The sensor 2 in this example has three rows of ultrasonic element 31, each row including eight ultrasonic elements 31. Differences in time are calculated under the following conditions:

$$V = 5900 \text{ [m/s]}$$

$$xij = (0.5 \times i - 0.25) \times 10^{-3} \text{ [m] } (i=1 \text{ to } 8)$$

$$yij = (1.3 \times j - 0.65) \times 10^{-3} \text{ [m] } (j=1 \text{ to } 3)$$

$$xf = 2 \times 10^{-3} \text{ [m]}$$

$$yf = 3 \times 10^{-3} \text{ [m]}$$

$$zf = 10 \times 10^{-3} \text{ [m]}$$

The above V, xij, yij, xf, yf, and zf are substituted into equations (2) and (3) and the differences in ultrasonic oscillation start time is calculated. A result shown in FIG. 11 is obtained by the calculation. If differences in ultrasonic oscillation start time are set as shown in FIG. 11, times taken for an ultrasonic wave to arrive at the focus point are equalized, increasing the signal strength.

Figure 12:
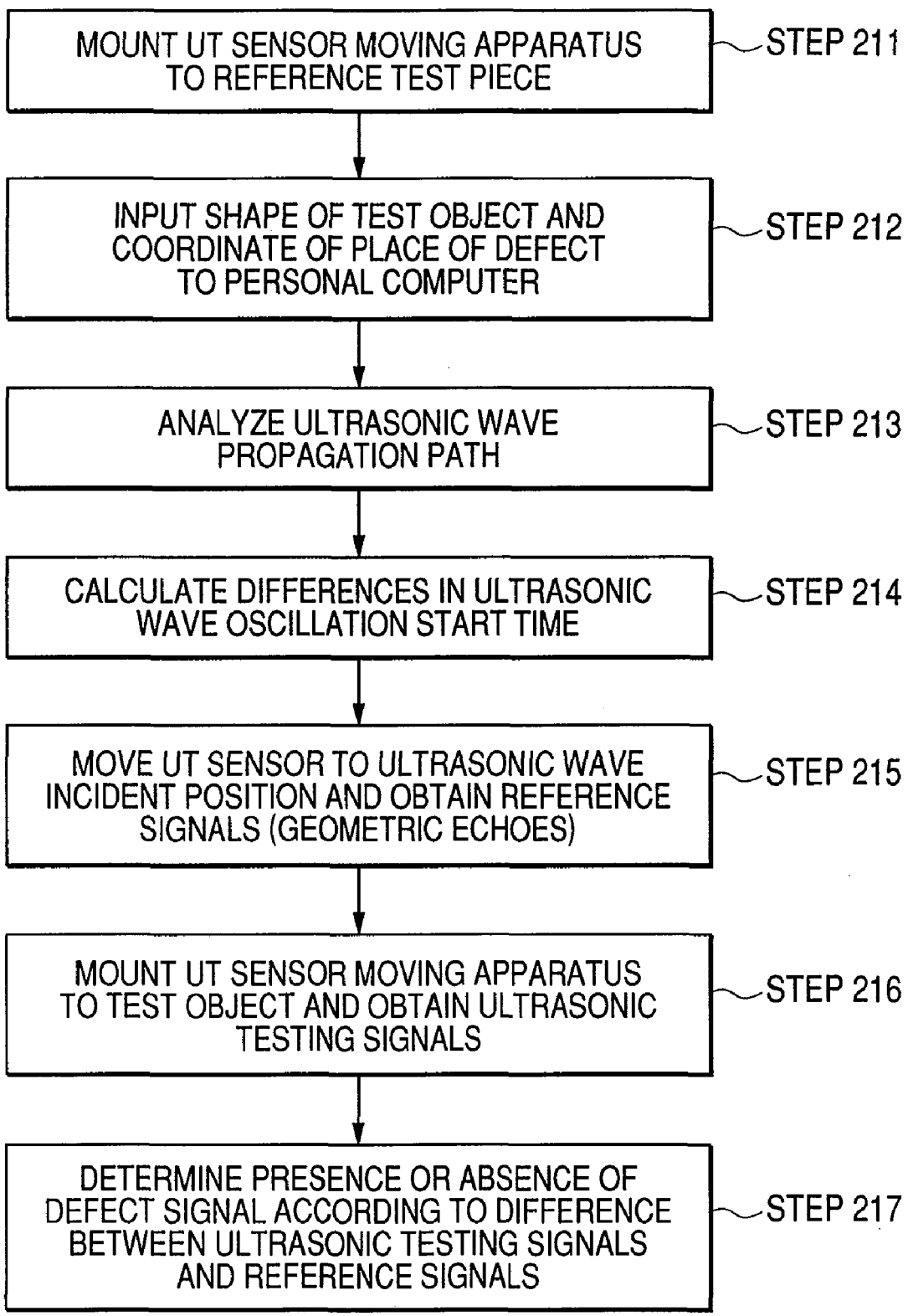
FIG. 12 is a flowchart showing procedure of an ultrasonic testing according to the embodiment 2.

FIG. 12 shows the ultrasonic testing steps in the embodiment 2.

In step 211, the UT sensor mounting apparatus is mounted to a reference test piece having the same size and same shape as the test object and no defect.

In step 212, the three-dimensional shape of the test object and the coordinates of a place of a defect in the test object are input to the personal computer 17.

In step 213, ultrasonic wave propagation paths are analyzed by using the three-dimensional geometric data.

Figure 13:
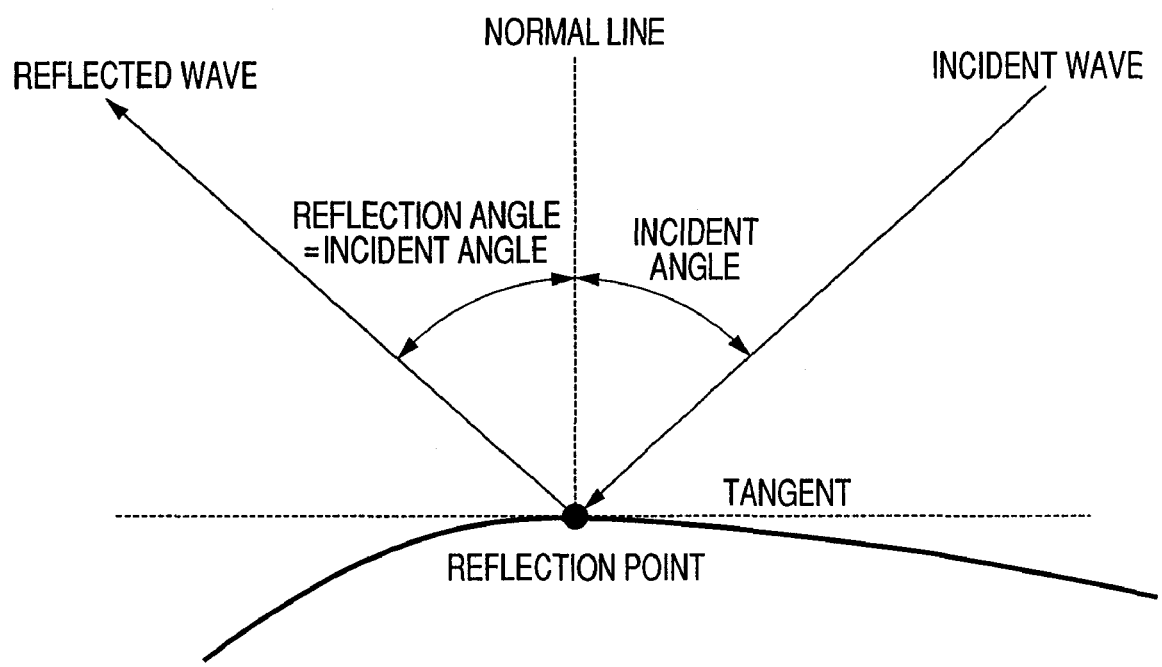
FIG. 13 is an explanatory drawing showing principle of ultrasonic wave propagation path analysis.

In step 211, ultrasonic wave propagation paths when an ultrasonic wave is emitted are calculated with the input coordinates of the defect place being set as a start point. The calculation is based on the fact that the ultrasonic wave propagates straight until it hits the external periphery of a fork and that when the ultrasonic wave hits the external periphery and reflects, the incident angle and reflection angle are symmetrical with respect to the normal line at the reflection point as shown in FIG. 13. Analysis is repeated with different ultrasonic wave emission angles measured from the coordinates of the defect position defect until this path reaches a side surface of the fork.

In step 214, coordinates of a central point of the UT sensor 2 and a distance of the ultrasonic wave propagation path to the side surface of the fork, obtained in step 213, are substituted in equations (4) and (5) to obtain Lij. The central point uses a point from which the ultrasonic wave is emitted to the side surface of the fork, obtained in step 213. The obtained Lij is substituted into equation (2) to calculate differences in ultrasonic wave oscillation start time among the ultrasonic elements 31 including in the UT sensor 2.

$$Lij' = ((xs-xij)^2 + (ys-yij)^2 + (zs-zij)^2 \quad (4)$$

$$Lij = (L1^2 + Lij'^2)^{1/2} \quad (5)$$

L1: Distance [m] of the ultrasonic wave propagation path to the side surface of the fork, obtained in step 213
Lij': Distance [m] between the central point of the sensor and the i-th element in the j-th row
  xs: x coordinate [m] of the central point of the sensor
  ys: y coordinate [m] of the central point of the sensor
  zs: z coordinate [m] of the central point of the sensor
  xij: x coordinate [m] of the i-th element in the j-th row
  yij: y coordinate [m] of the i-th element in the j-th row
  zij: z coordinate [m] of the i-th element in the j-th row In step 215, the UT sensor 2 is moved to the ultrasonic wave incident position on the reference test piece and the reference signals (geometric echoes) are obtained.

In step 216, the UT sensor moving apparatus is mounted to the test object and an ultrasonic testing signal is obtained.

In step 217, the reference signals are subtracted from the ultrasonic testing signals and determine the presence or absence of a defect is determined according to whether the value obtained by subtracting the reference signal from the ultrasonic testing signal is plus value. If the value obtained is plus value, it indicates that there is a defect.

Figure 14:
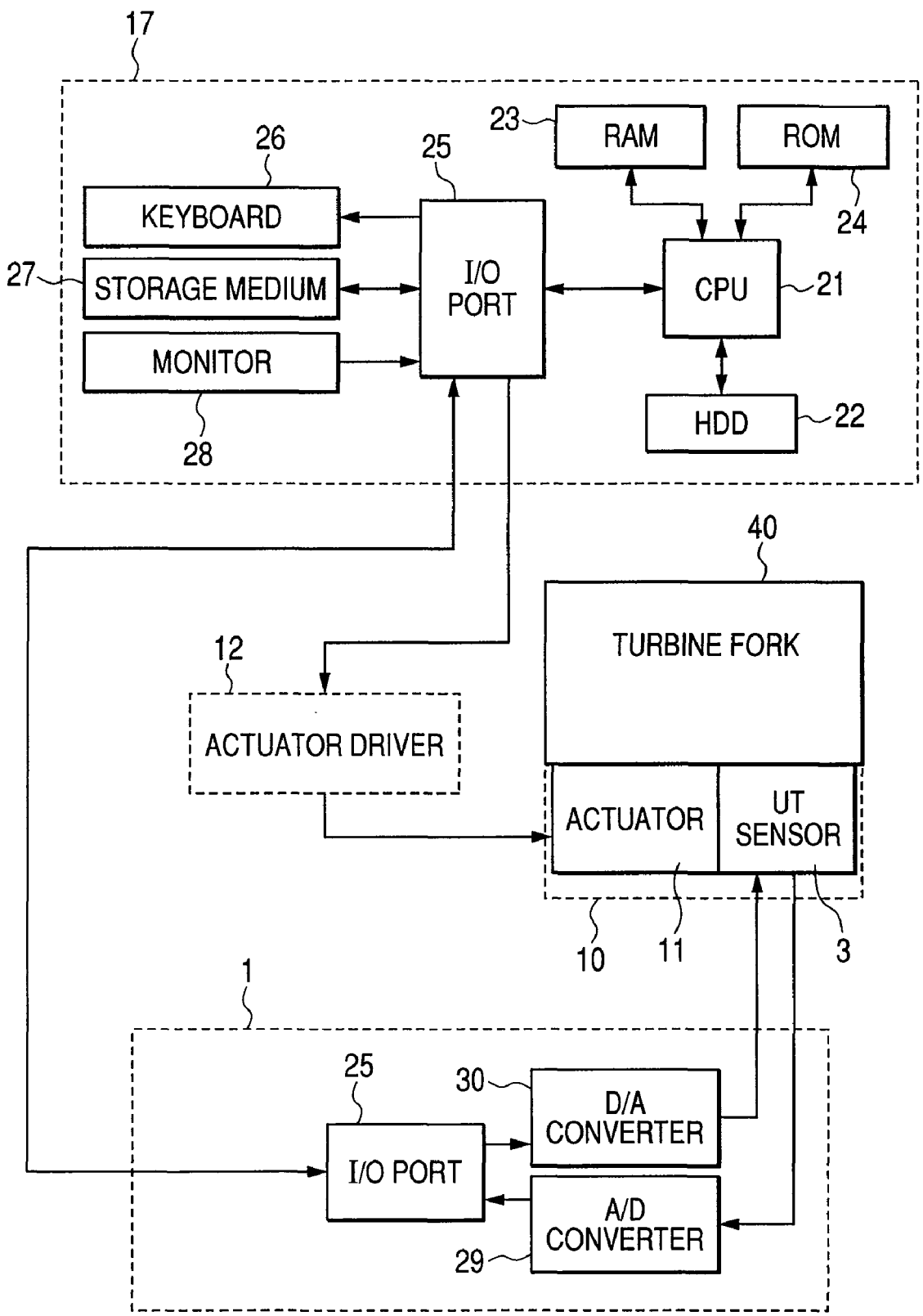
FIG. 14 is an explanatory drawing showing the flow of signal transmission according to the embodiment 2.
Figure 15A:
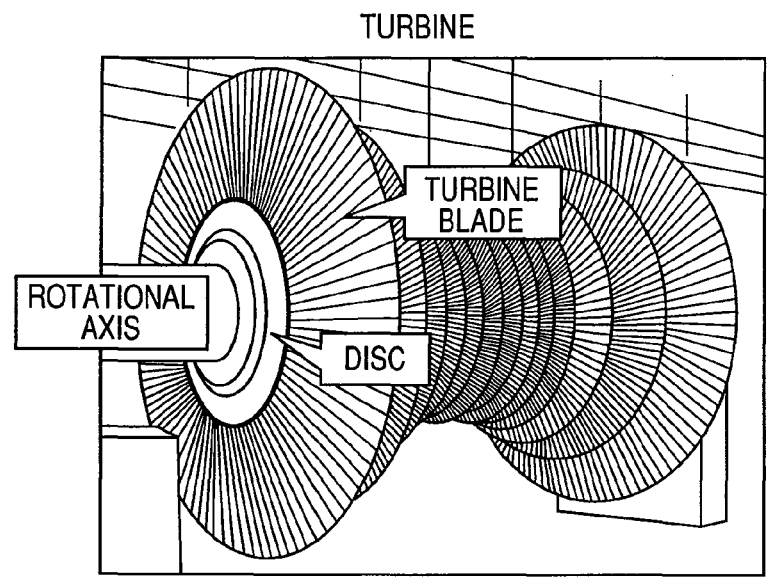
FIGS. 15A, 15B and 15C are a structural diagram showing a turbine and a turbine fork.
Figure 15B:
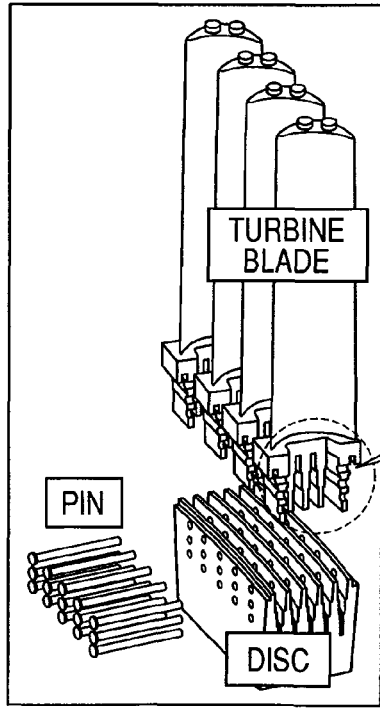
Figure 15C:
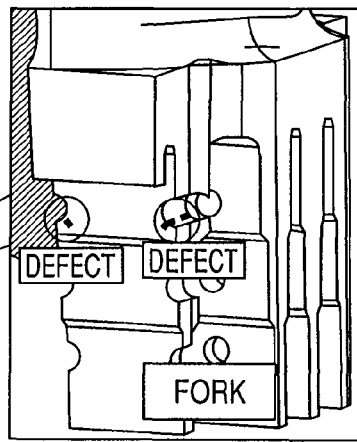
Figure 16:
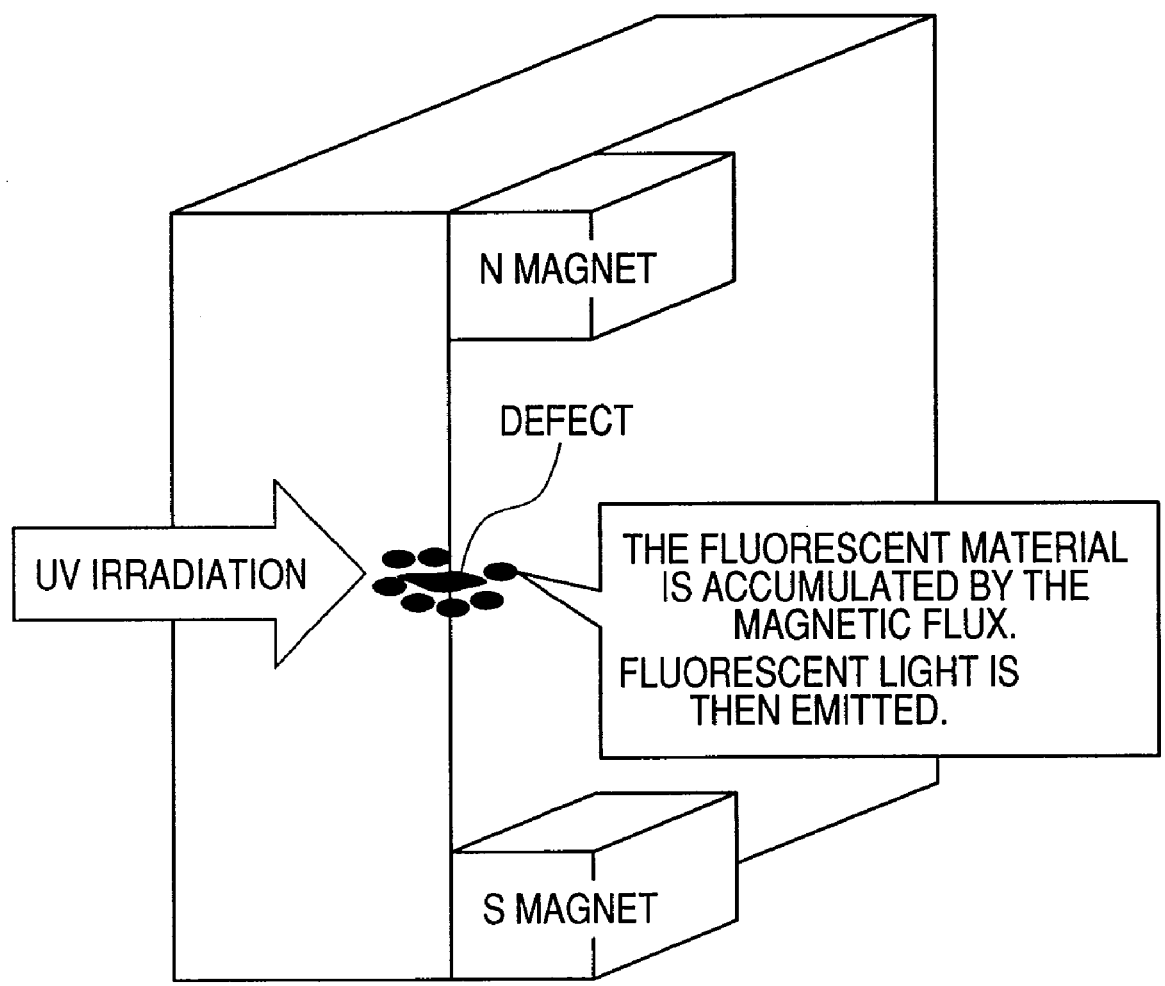
FIG. 16 is an explanatory drawing showing a conventional turbine fork inspection method.
Figure 17A:
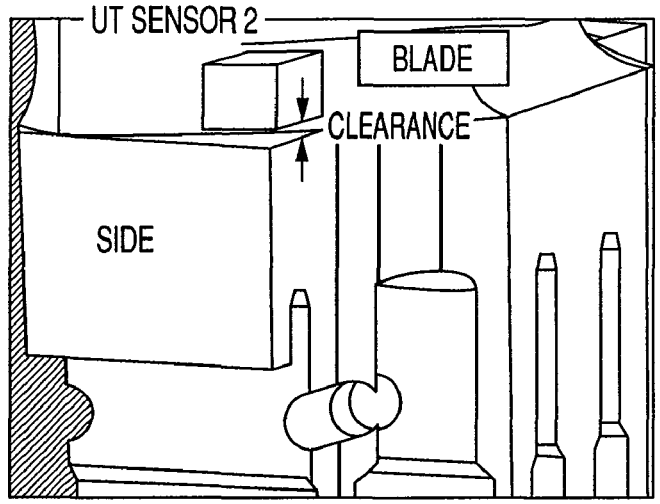
FIGS. 17A and 17B is an explanatory drawing showing problems in a turbine fork inspection based on ultrasonic testing.
Figure 17B:
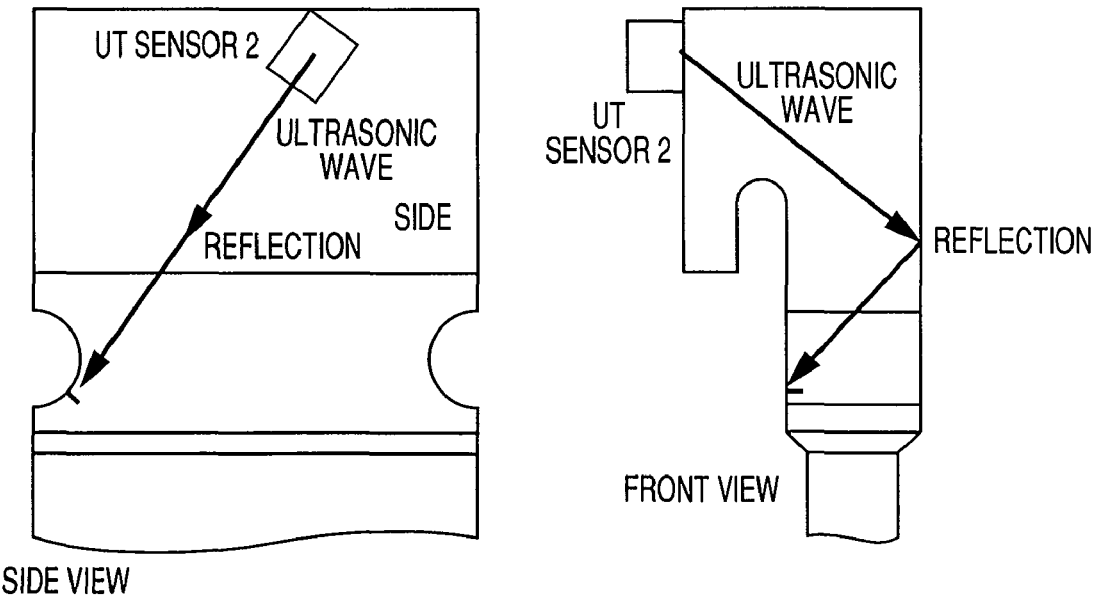

FIG. 14 shows how signals in the embodiment 2 flow.

The three-dimensional geometric data on the test object is input from a storage medium 27 such as a magneto-optical disc (MO), compact disc (CD), or digital versatile disc (DVD), and the coordinates of a position of a defect are input from the keyboard 26. The three-dimensional geometric data and the coordinates of the defect position are passed to the CPU 21 through an I/O port 25 in the personal computer 17. The CPU 21 then calculates the ultrasonic wave propagation path and a difference in ultrasonic wave oscillation start time.

The UT sensor 2 is moved to the ultrasonic wave incident position based on the analysis result for the ultrasonic wave propagation path by supplying power to the actuators 11 through the I/O port 25 in the personal computer 17 and the actuator driver 12. An ultrasonic wave is sent into the test object (turbine fork) by applying a voltage according to the differences in ultrasonic wave oscillation start time to the ultrasonic elements 31 through the I/O port 25 in the personal computer 17, and an I/O port 25 and a D/A converter 30 in the ultrasonic test equipment 1. The ultrasonic wave reflected at a concavity and convexity on the test object is converted by the UT sensor 2 into a voltage. This converted voltage is transmitted to the CPU 21 through an A/D converter 29 and the I/O port 25 in the ultrasonic test equipment 1, and the I/O port 25 in the personal computer 17.

The sensor position, the differences in ultrasonic wave oscillation start time, and ultrasonic testing results are stored in at least one of a hard disc drive 22 (HDD), a random access memory (RAM) 23, and a read-only memory (ROM) 24 by the CPU 21. The CPU 21 also subtracts the reference signals from the ultrasonic testing signals and displays the result on a monitor 28 through the I/O port 25 in the personal computer 17.

As described above, in the present embodiment, since the location to mount the UT sensor 2 and the incident angle of an ultrasonic wave are obtained through analysis, and movement of the UT sensor 2 and ultrasonic testing are automatically performed, the inspection time of the turbine forks is further shortened, as compared with the embodiment 1.

What is claimed is:

1. An ultrasonic testing apparatus for a turbine fork of a turbine blade joined to a turbine disc, comprising:
   an ultrasonic testing sensor for sending ultrasonic waves and receiving reflected waves of the ultrasonic waves;
   a sensor mounting apparatus for mounting said ultrasonic testing sensor on a flat portion of a side surface of said turbine fork with said turbine blade joined to said turbine disc;
   an ultrasonic testing equipment for inspecting internal and external surfaces of said turbine fork by using the reflected waves, which are received by said ultrasonic testing sensor, from the internal surface of said turbine fork;
   wherein said sensor mounting apparatus has a pair of fixing pawls set to said turbine blade, a magnet holder being fixed on said turbine disc by magnetic force, a first rotating member attached to said magnet holder, an arm member, in which a through-groove is formed in a longitudinal direction of itself, turned around said first rotating member, a second rotating member, by which said ultrasonic testing sensor is moved along the longitudinal direction of said arm member, installed to said arm member in such a way that it passes through the through-groove, and a spring pressing said ultrasonic testing sensor against said flat portion of said side surface of said turbine fork together with said arm member, and surrounding said first rotating member.

2. The ultrasonic testing apparatus for a turbine fork according to claim 1, wherein said ultrasonic testing equipment uses a predetermined ultrasonic wave generated in said turbine fork as a reference signal, and detects the reflected wave from a defect by comparing a detected ultrasonic wave with the reference signal.

3. An ultrasonic testing apparatus for a turbine fork of a turbine blade joined to a turbine disc, comprising:
   an ultrasonic testing sensor for sending ultrasonic waves and receiving reflected waves of the ultrasonic waves;
   a sensor mounting apparatus for mounting said ultrasonic testing sensor on a flat portion of a side surface of said turbine fork with said turbine blade joined to said turbine disc;
   an ultrasonic testing equipment for inspecting internal and external surfaces of said turbine fork by using the reflected waves, which are received by said ultrasonic testing sensor, from the internal surface of said turbine fork;
   wherein first graduations exist on a surface of said arm member along the longitudinal direction of the through-groove beside the through-groove; and second graduations exist on a surface of one end of said first rotating member; and third graduations exist on a surface of one end of said second rotating member.

4. The ultrasonic testing apparatus for a turbine fork according to claim 3, wherein said ultrasonic testing equipment uses a predetermined ultrasonic wave generated in said turbine fork as a reference signal, and detects the reflected wave from a defect by comparing a detected ultrasonic wave with the reference signal.

5. An ultrasonic testing for a turbine fork with a turbine blade joined to a turbine disc, comprising:
   an ultrasonic testing sensor for sending ultrasonic waves and receiving reflected waves of the ultrasonic waves;

a pair of fixing pawls and a magnet holder for setting said ultrasonic testing sensor on a flat portion, which is perpendicular to an axial direction of a turbine disc, parallel with a radial direction of said turbine disc, and parallel with a longitudinal direction of a turbine blade joined to said turbine disc, on a side surface of said turbine fork with said turbine blade;

a first rotating member attached to said magnet holder;

an arm member, in which a through-groove is formed in a longitudinal direction of itself, turned around said first rotating member;

a second rotating member, by which said ultrasonic testing sensor is moved along the longitudinal direction of said arm member, installed to said arm member in such a way that it passes through the through-groove;

an ultrasonic testing sensor mounting tool having graduations and installed to said first rotating member, said arm member and said second rotating member; and an ultrasonic testing equipment connected electrically to said ultrasonic testing sensor.

6. An ultrasonic testing method for a turbine fork of a turbine blade joined to a turbine disc, comprising the steps of:

obtaining at least one reference signal by performing ultrasonic testing for a reference test object having no defect and of the same size as a test object part of said turbine fork by an ultrasonic testing apparatus, comprising:

an ultrasonic testing sensor for sending ultrasonic waves and receiving reflected waves of the ultrasonic waves;

a pair of fixing pawls and a magnet holder for setting said ultrasonic testing sensor on a flat portion, which is perpendicular to an axial direction of a turbine disc, parallel with a radial direction of said turbine disc, and parallel with a longitudinal direction of a turbine blade joined to said turbine disc, of a side surface of said turbine fork with said turbine blade;

a first rotating member attached to said magnet holder;

an arm member, in which a through-groove is formed in a longitudinal direction of itself, turned around said first rotating member;

a second rotating member, by which said ultrasonic testing sensor is moved along the longitudinal direction of said arm member, installed to said arm member in such a way that it passes through the through-groove;

an ultrasonic testing sensor mounting tool having graduations installed to said first rotating member, said arm member and said second rotating member; and an ultrasonic testing equipment connected electrically to said ultrasonic testing sensor, setting said ultrasonic testing sensor on said flat portion on the side surface of said turbine fork with said turbine blade joined to said turbine disc by using said sensor mounting apparatus;

obtaining ultrasonic testing signals by performing ultrasonic testing for said test object part of said turbine fork by said set ultrasonic testing sensor; and determining whether a defect is present by comparing the ultrasonic testing signals with the reference signals.

7. An ultrasonic testing method for a turbine fork of a turbine blade joined to a turbine disc, comprising the steps of:

obtaining reference signals by performing ultrasonic testing for a reference test object having no defect and of the same size as a test object part of said turbine fork by an ultrasonic testing apparatus, comprising:

an ultrasonic testing sensor for sending ultrasonic waves and receiving reflected waves of the ultrasonic waves;

a sensor mounting apparatus for mounting said ultrasonic testing sensor on a flat portion of a side surface of said turbine fork with said turbine blade joined to said turbine disc; and an ultrasonic testing equipment for inspecting internal and external surfaces of said turbine fork by using the reflected waves, which is received by said ultrasonic testing sensor, from the internal surface of said turbine fork;

wherein said sensor mounting apparatus has a pair of fixing pawls set to said turbine blade, a magnet holder being fixed on said turbine disc by magnetic force, a first rotating member attached to said magnet holder, an arm member, in which a through-groove is formed in a longitudinal direction of itself, turned around said first rotating member, a second rotating member, by which said ultrasonic testing sensor is moved along the longitudinal direction of said arm member, installed to said arm member in such a way that it passes through the through-groove, and a spring pressing said ultrasonic testing sensor against said flat portion of said side surface of said turbine fork together with said arm member, and surrounding said first rotating member, setting said ultrasonic testing sensor on said flat portion of said side surface of said turbine fork with said turbine blade joined to said turbine disc by using said sensor mounting apparatus;

obtaining ultrasonic testing signals by performing ultrasonic testing for said test object part of said turbine fork by said set ultrasonic testing sensor; and determining whether a defect is present by comparing the ultrasonic testing signals with the reference signals.

* * * * *